(12) United States Patent
Iuchi et al.

(10) Patent No.: US 9,204,632 B2
(45) Date of Patent: Dec. 8, 2015

(54) PROCESS FOR PRODUCING MICROCAPSULE FORMULATION AND MICROCAPSULE FORMULATION PRODUCED BY SAME PROCESS

(75) Inventors: Seiji Iuchi, Chuo-ku (JP); Rie Takabe, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 153 days.

(21) Appl. No.: 13/879,163

(22) PCT Filed: Oct. 26, 2011

(86) PCT No.: PCT/JP2011/075236
§ 371 (c)(1),
(2), (4) Date: Apr. 12, 2013

(87) PCT Pub. No.: WO2012/057360
PCT Pub. Date: May 3, 2012

(65) Prior Publication Data
US 2013/0202671 A1 Aug. 8, 2013

(30) Foreign Application Priority Data
Oct. 28, 2010 (JP) .................................. 2010-242058

(51) Int. Cl.
*A01N 25/28* (2006.01)
*A01N 43/78* (2006.01)
*B01J 13/16* (2006.01)
*A01N 51/00* (2006.01)

(52) U.S. Cl.
CPC ................. *A01N 25/28* (2013.01); *A01N 43/78* (2013.01); *B01J 13/16* (2013.01)

(58) Field of Classification Search
CPC ................................ A01N 25/28; A01N 53/00
See application file for complete search history.

(56) References Cited

U.S. PATENT DOCUMENTS

| 2009/0081307 | A1 | 3/2009 | Tsuda |
| 2009/0142406 | A1 | 6/2009 | Tanedani |
| 2009/0162409 | A1* | 6/2009 | Tanedani ....................... 424/408 |
| 2009/0182015 | A1 | 7/2009 | Kanayama |
| 2009/0226496 | A1* | 9/2009 | Mulqueen et al. ............ 424/408 |
| 2012/0065070 | A1 | 3/2012 | Iuchi et al. |

FOREIGN PATENT DOCUMENTS

| EP | 1961303 A1 | 8/2008 |
| EP | 2025229 A1 | 2/2009 |
| JP | 02-275803 A | 11/1990 |
| JP | 08-099805 A | 4/1996 |
| JP | 2000-247821 A | 9/2000 |
| JP | 2005-170956 A | 6/2005 |
| JP | 2005170956 A * | 6/2005 |
| JP | 2007-186496 A | 7/2007 |
| JP | 2007-186497 A | 7/2007 |
| JP | 2007-320914 A | 12/2007 |
| JP | 2009-062298 A | 3/2009 |
| JP | 2010-275238 A | 12/2010 |
| WO | 03051116 A1 | 6/2003 |

OTHER PUBLICATIONS

Derwent abstract of JP 2005/170956 A, Jun. 2005.*
English Translation of JP 2005/170956 A from Espacenet, machine translation, Jun. 2005.*
Extended Search Report dated Apr. 7, 2014 in European Patent Application No. 11836492.6.
International Preliminary Report on Patentability and Written Opinion dated Apr. 30, 2013 in International Application No. PCT/JP2011/075236 to Sumitomo Chemical Co., Ltd.
Notice of Reasons for Rejection issued Aug. 19, 2014 in corresponding Japanese Patent Application No. 2010-242058 with partial English translation.

* cited by examiner

*Primary Examiner* — Sean Basquill
*Assistant Examiner* — Mark V Stevens
(74) *Attorney, Agent, or Firm* — Sughrue Mion, PLLC

(57) ABSTRACT

The present invention is intended to provide a technique for delaying timing for releasing an agricultural chemical compound from a microcapsule formulation which contains the agricultural chemical compound in at least one compound from the group of consisting of ester compounds and aromatic hydrocarbon compounds. A microcapsule formulation produced by the following process is more effectively controlled in release of an agricultural chemical compound therefrom, than any of the existing microcapsule formulations. This production process comprises the steps of
(1) maintaining a mixture of an agricultural chemical compound (a), at least one compound (b) selected from the group consisting of ester compounds and aromatic hydrocarbon compounds, except for the compounds of the formula (I):

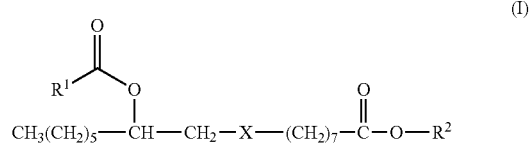

(I)

(wherein X represents —$CH_2$—$CH_2$— or —CH=CH—; $R^1$ represents a $C_1$-$C_4$ alkyl group; and $R^2$ represents a $C_1$-$C_4$ alkyl group), and a polyisocyanate (c) at a temperature of from 20 to 80° C. for 3 hours or longer;
(2) adding the resulting mixture to an aqueous solution which contains a polyol or a polyamine, to form liquid droplets of the mixture in the aqueous solution;
(3) forming coatings of a polyurethane or a polyurea around the liquid droplets.

4 Claims, No Drawings

PROCESS FOR PRODUCING MICROCAPSULE FORMULATION AND MICROCAPSULE FORMULATION PRODUCED BY SAME PROCESS

CROSS REFERENCE TO RELATED APPLICATIONS

This application is a National Stage of International Application No. PCT/JP2011/075236, filed on Oct. 26, 2011, which claims priority from Japanese Patent Application No. 2010-242058, filed on Oct. 28, 2010, the contents of all of which are incorporated herein by reference in their entirety.

TECHNICAL FIELD

The present application is filed claiming the priority of Japanese Patent Application No. 2010-242058 filed on Oct. 28, 2010 under the Paris Convention, the entire content of which is incorporated herein by reference.

The present invention relates to a process for producing a microcapsule formulation and to a microcapsule formulation produced by the same process.

BACKGROUND ART

There are known microcapsules which are resin-coated liquid droplets that an agricultural chemical compound is suspended in a liquid such as diisodecyl adipate (Patent Document 1).

PRIOR ART LITERATURE

Patent Document 1: JP-A-H08-099805

SUMMARY OF INVENTION

A microcapsule formulation of an agricultural chemical compound is a formulation intended to control timing for releasing an agricultural chemical compound in the formulation.

The present invention provides a technique for delaying timing for releasing an agricultural chemical compound in a microcapsule formulation which contains the agricultural chemical compound.

The present inventors have found out that the following process is effective to delay timing for releasing an agricultural chemical compound from microcapsules: that is, in the production of a microcapsule formulation, a mixture of an agricultural chemical compound, at least one kind selected from the group consisting of ester compounds and aromatic hydrocarbon compounds, and a polyisocyanate is maintained at a temperature of from 20 to 80° C. for 3 hours or longer; and then, the resulting mixture is used for production of a microcapsule formulation.

The present invention provides the following.

[1] A process for producing a microcapsule formulation, comprising the steps of
(1) maintaining a mixture of the following constitutive components (a), (b) and (c) at a temperature of from 20 to 80° C. for 3 hours or longer;
(2) adding the resulting mixture to an aqueous solution which contains a polyol or a polyamine, to thereby form liquid droplets of the mixture in the aqueous solution; and
(3) forming coatings of a polyurethane or a polyurea around the liquid droplets:
the constitutive component (a):
an agricultural chemical compound;
the constitutive component (b):
at least one kind selected from the group consisting of ester compounds and aromatic hydrocarbon compounds, except for the following formula (I):

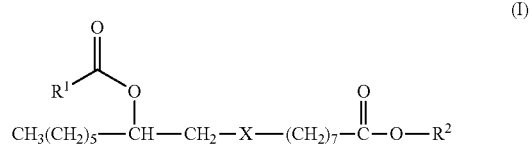

wherein X represents —$CH_2$—$CH_2$— or —CH=CH—; $R^1$ represents a $C_1$-$C_4$ alkyl group; and $R^2$ represents a $C_1$-$C_4$ alkyl group); and
the constitutive component (c):
a polyisocyanate.
[2] The process described in the item [1], wherein a weight ratio of the constitutive component (a) to the constitutive component (b), [the constitutive component (a)/the constitutive component (b)], is from 10/100 to 100/100.
[3] The process described in the item [1] or [2], wherein the constitutive component (b) is at least one kind selected from the group consisting of adipates and aromatic hydrocarbon compounds.
[4] The process described in the item [1] or [2], wherein the constitutive component (b) is at least one kind selected from the group consisting of diisobutyl adipate, diisodecyl adipate and methyl naphthalene.
[5] The process described in any one of the items [1] to [4], wherein the agricultural chemical compound is a solid agricultural chemical compound.
[6] The process described in any one of the items [1] to [4], wherein the agricultural chemical compound is a neonicotinoid compound.
[7] The process described in any one of the items [1] to [4], wherein the agricultural chemical compound is clothianidin.
[8] A microcapsule formulation produced by the process described in any one of the items [1] to [7].

By any of the processes for producing microcapsule formulations according to the present invention, there can be obtained a microcapsule formulation more effectively controlled in release of an agricultural chemical compound than any of the existing microcapsule formulations.

DESCRIPTION OF EMBODIMENTS

The process for producing a microcapsule formulation according to the present invention comprises
(1) a first step of maintaining a liquid mixture of the constitutive components (a), (b) and (c) at a temperature of from 20 to 80° C. for 3 hours or longer;
(2) a second step of adding the resulting mixture to an aqueous solution which contains a polyol or a polyamine, thereby forming liquid droplets of the mixture in the aqueous solution; and
(3) a third step of forming coatings of a polyurethane or a polyurea around the liquid droplets.

In the present invention, a solid agricultural chemical compound is preferably used as the constitutive component (a), i.e., the agricultural chemical compound. The solid agricultural chemical compound referred to in the present invention means a compound which exhibits an agrichemical activity and which has a melting point of 15° C. or higher, preferably 50° C. or higher. A more preferable solid agricultural chemical compound in the present invention is a compound which exhibits an agrichemical activity and which has a melting point of 15° C. or higher, preferably 50° C. or higher and has a solubility of 5% by weight or less in the constitutive component (b).

Examples of the constitutive component (a), i.e., the agricultural chemical compound, include insecticidal compounds, bactericidal compounds, herbicidal compounds, insect growth-regulating compounds, plant growth-regulating compounds and rejectant compounds.

Examples of the insecticidal compounds include carbamate compounds such as propoxur, isoprocarb, xylylcarb, metolcarb, XMC, carbaryl, pyrimicarb, carbofuran, methomyl, fenoxycarb, alanycarb and metoxadiazone; organic phosphorus compounds such as acephate, phenthoate, vamidothion, trichlorfon, monocrotophos, tetrachlorvinphos, dimethylvinphos, phosalone, chlorpyrifos, chlorpyrifos-methyl, pyridafenthion, quinalphos, methidathion, methamidophos, dimethoate, fermothion, azinphos-ethyl, azinphos-methyl and salithion; neonicotinoid compounds such as imidacloprid, nitenpyram, acetamiprid, clothianidin and thiamethoxam; 4-chloro-2-(2-chloro-2-methylpropyl)-5-(6-iode-3-pyridylmethoxy)pyridazine-3(2H)-one; cartap; buprofezin; thiocyclam; bensultap; fenoxycarb; fenazaquin; fenpyroximate; pyridaben; hydramethylnon; thiodicarb; chlorfenapyr; fenpyroximate; pymetrozine; pyrimidifen; tebufenozide; tebufenpyrad; triazamate; indoxacarb; sulfluramid; milbemectin; avermectin; and paradichlorobenzene.

Examples of the bactericidal compounds include benzimidazole compounds such as benomyl, carbendazim, thiabendazole and thiophanate-methyl; phenylcarbamate compounds such as diethofencarb; dicarboxylmide compounds such as prosymidone, iprodione and vinclozolin; azole compounds such as diniconazole, propenazole, epoxyconazole, tebuconazole, diphenoconazole, cyproconazole, flusilazole and triadimefon; acylalanine compounds such as metalaxyl; carboxyamide compounds such as furametpyr, mepronil, flutolanil and trifluzamide; organic phosphorus compounds such as tolclophos-methyl, fosetylaluminum and pyrazophos; anilinopyrimidine compounds such as pyrimethanil, mepanipyrim and cyprodinyl; cyanopyrrole compounds such as fludioxonil and fenpiclonil; chlorothalonil; manzeb; captan; folpet; tricyclazole; pyroquilon; probenazole; phthalide; cymoxanil; dimethomorph; famoxadone; oxolinic acid and a salt thereof; fluazinam; ferimzone; diclocymet; chlobenthiazone; isovaledione; tetrachloroisophthalo-nitrile; thiophthalimidoxy bisphenoxyarsine; and 3-iode-2-propylbutylcarbamate.

Examples of the herbicidal compounds include triazine compounds such as atrazine, metribuzin; urea compounds such as fluometuron and isoproturon; hydroxybenzonitrile compounds such as bromoxynil and ioxynil; 2,6-dinitroaniline compounds such as pendimethalin and trifluralin; aryloxyalkanoic acid compounds such as 2,4-D, dicamba, fluoroxypyr and mecoprop, and salts thereof; sulfonylurea compounds such as bensulfuron-methyl, metsulfuron-methyl, nicosulfuron, primisulfuron-methyl and cyclosulfamron; imidazolinone compounds such as imazapyr, imazaquin and imazethapyr, and salts thereof; sulfentrazone; paraquat; flumetsulam; triflusulfuron-methyl; fenoxaprop-p-ethyl; cyhalofop-butyl; diflufenican; norflurazon; isoxaflutole; glufosinate ammonium salt; glyphosate salt; bentazone; benthiocarb; mefenacet; propanil; fluthiamide; flumiclorac-pentyl; and flumioxazin.

Examples of the insect growth-regulating compounds include benzoylurea compounds such as diflubenzuron, chlorfluazuron, lufenuron, hexaflumuron, flufenoxuron, flucycloxuron, cyromazine, diafenthiuron, hexythiazox, novalron, teflubenzuron, triflumuron, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl] urea and 1-(2,6-difluorobenzoyl)-3-[2-fluoro-4-(1,1,2,2-tetrafluoroethoxy)phenyl]urea; and pyriproxyfen. Examples of the plant growth-regulating compounds include hydrazide maleate, chlormequat, ethephon, gibberelin, mepiquat chloride, thidiazuron, inabenfide, paclobutrazol and uniconazole. Examples of the rejectant compounds include 1S,3R,4R,6R-carane-3,4-diol and dipropyl 2,5-pyridine dicarboxylate.

In the present invention, the constitutive component (b) is in the form of a liquid at a maintaining temperature specified in the first step of the production process of the present invention. The constitutive component (b) is hard to admix with water and is suitable to dissolve an agricultural chemical compound or disperse or suspend the agricultural chemical compound. Examples of the ester compounds as the constitutive component (b) include carboxylates (i.e. carboxylic acid esters) such as saturated fatty acid esters, unsaturated carboxylates, hydroxy acid esters, aromatic carboxylates and dicarboxylates. Examples of the saturated fatty acid esters are acetates (i.e. acetic acid esters) and laurates (i.e. lauric acid esters). Examples of the unsaturated carboxylates are oleates (i.e. oleic acid esters). Examples of the aromatic carboxylates are phthalates (i.e. phthalic acid esters) and salicylates (i.e. salicylic acid esters). Examples of the dicarboxylates are adipates (i.e. adipic acid esters). Examples of the adipates are dialkyl adipates such as dimethyl adipate, diethyl adipate, dipropyl adipate, diisopropyl adipate, diisobutyl adipate, dihexyl adipate, bis(2-ethylhexyl) adipate, dioctyl adipate, diisononyl adipate, didecyl adipate and diisodecyl adipate, and mixtures of these dialkyl adipates (e.g., mixtures of di-n-alkyl adipates such as a mixture of dihexyl adipate, dioctyl adipate and didecyl adipate); and vinyl adipates. Examples of the aromatic hydrocarbon compound as the constitutive component (b) include methyl naphthalene, dimethyl naphthalene, ethyl naphthalene, propyl naphthalene, butyl naphthalene, phenyl xylylethane, toluene, xylene and dimethylmonoisopropyl naphthalene.

In the production process of the present invention, mixtures of the above-described ester compounds with the above-described aromatic hydrocarbon compounds may be used.

In the present invention, examples of the constitutive component (c), i.e., the polyisocyanate, include hexamethylene diisocyanate; an adduct of hexamethylene diisocyanate and trimethylolpropane; a biuret condensate of three molecules of hexamethylene diisocyanate; an adduct of tolylene diisocyanate and trimethylolpropane; an isocyanurate condensate of tolylene diisocyanate; an isocyanurate condensate of hexamethylene diisocyanate; an isocyanurate condensate of isophoronediisocyanate; an isocyanate prepolymer in which one isocyanate moiety of hexamethylene diisocyanate constitutes an isocyanurate form together with two molecules of tolylene diisocyanate, and in which the other isocyanate moiety thereof constitutes an isocyanurate form together with two molecules of the other hexamethylene diisocyanate; 4,4'-methylenebis-(cyclohexylisocyanate); and trimethylhexamethylene diisocyanate.

In the present invention, a weight ratio of the constitutive component (a) to the constitutive component (b) is usually from 10/100 to 100/100, preferably from 20/100 to 40/100.

An amount of the polyisocyanate to be used in the present invention is determined usually according to an amount of coatings on microcapsules to be produced. An amount of the coatings on the microcapsules to be produced is usually from 5 to 45% by weight, preferably from 10 to 30% by weight, based on the weight of the entire microcapsules. An amount of the polyisocyanate to be used in the present invention is usually from 25 to 90% by weight, preferably from 40 to 70% by weight, based on the weight of the coatings on the microcapsules.

The constitutive component (a), i.e., the agricultural chemical compound, is dissolved or suspended in the constitutive component (b).

In case where the agricultural chemical component is dissolved in the constitutive component (b), a mixture of the agricultural chemical compound (or the constitutive component (a)), the constitutive component (b) and the polyisocyanate (or the constitutive component (c)) in the first step can be prepared by mixing the agricultural chemical compound, the constitutive component (b) and the polyisocyanate.

In case where the agricultural chemical compound is a solid agricultural chemical compound, the solid agricultural chemical compound is suspended in the constitutive component (b), depending on a solubility of the solid agricultural chemical compound in the constitutive component (b) and a weight ratio of the solid agricultural chemical compound to the constitutive component (b). When the solid agricultural chemical compound is suspended in the constitutive component (b), for example, a mixture of the solid agricultural chemical compound, the constitutive component (b) and the polyisocyanate in the first step can be prepared by pulverizing the solid agricultural chemical compound in the constitutive component (b) to obtain a liquid suspension, and adding the polyisocyanate to the liquid suspension.

To pulverize the solid agricultural chemical compound in the constitutive component (b), the solid agricultural chemical compound and optionally beads or the like for pulverization are added to the constitutive component (b), and the resulting mixture is subjected to wet pulverization with a pulverizer. Examples of the pulverizer to be used are mills such as a bead mill, ball mill and rod mill, and a rotor stator homogenizer. Specific examples of the pulverizer are Atliter (from Mitsui Miike Machinery Co., Ltd.), Dynomill (from WILLY A. BACHOFEN AG. MASHINENFABRIK), Colloid Mill (from PRIMIX) and Pearl Mill (from Ashizawa Tekko). A specific example of the rotor stator homogenizer is Polytron Homegenizer (from KINEMATICA AG).

When the solid agricultural chemical compound is subjected to wet pulverization in the presence of the constitutive component (b), particles of the solid agricultural chemical compound are evenly dispersed, and the pulverized particles do not agglomerate to one another, and further, a viscosity of the liquid suspension during the wet pulverization is not so increased. Therefore, a power load on the pulverizer is small, and thus, the production is facilitated.

The operation of pulverizing the solid agricultural chemical compound in the constitutive component (b) may include two or more operations. For example, to pulverize the solid agricultural chemical compound in the constitutive component (b), the solid agricultural chemical compound may be coarsely milled in the first operation, and the coarsely milled compound further may be finely milled. To pulverize the solid agricultural chemical compound in the constitutive component (b) by two operations, there is employed, for example, a method with the use of a rotor stator homogenizer as a pulverizer in the first operation and a mill in the second operation.

In case where the solid agricultural chemical compound is suspended in the constitutive component (b), particle diameters of the solid agricultural chemical compound particles suspended in the constitutive component (b) are usually 10 µm or less, preferably from 1 to 5 µm, in terms of volume median diameter. In the solid agricultural chemical compound particles suspended in the constitutive component (b), a total volume of the solid agricultural chemical compound particles with particle diameters of 10 µm or more is preferably 10% or less of a total volume of the entire solid agricultural chemical compound particles.

In the present invention, the mixture of the agricultural chemical compound, the constitutive component (b) and the polyisocyanate further may contain other organic solvent. Examples of the organic solvent include aliphatic hydrocarbons such as trimethylpentane; ethers such as 2-ethylhexyl ether; mineral oils such as machine oil; and vegetable oils such as cotton seed oil. An amount of the organic solvent, if contained, is usually ½ or less, preferably ⅗ or less, more preferably ¼ or less in a weight ratio to the constitutive component (b).

In the first step of the production process of the present invention, the above-described mixture of the agricultural chemical compound, the constitutive component (b) and the polyisocyanate is maintained at a temperature of from 20 to 80° C. for 3 hours or longer. An upper limit of this maintaining time is usually 48 hours or shorter, while not limited thereto. A preferable maintaining time is 5 hours or longer, and a preferable maintaining temperature is from 20 to 60° C.

This mixture may be stirred or may be left to stand still, while the mixture is maintained at a temperature of from 20 to 80° C. In the first step, generally, the mixture is so controlled as to be maintained at a temperature of from 20 to 80° C.

In the second step of the production process of the present invention, the mixture obtained in the first step is added to an aqueous solution which contains a polyol or a polyamine to form liquid droplets of the mixture in the aqueous solution.

In case where an aqueous solution which contains a polyol is used in this step, microcapsules having polyurethane coatings formed thereon are produced. In case where an aqueous solution which contains a polyamine is used in this step, microcapsules having polyurea coatings formed thereon are produced.

The polyol-containing aqueous solution is prepared, for example, by mixing water with a polyol. The polyamine-containing aqueous solution is prepared, for example, by mixing water with a polyamine or a salt of polyamine.

Examples of the polyol to be used in the present invention include ethylene glycol, propylene glycol, butylene glycol and cyclopropylene glycol. Examples of the polyamine to be used in the present invention include ethylene diamine, hexamethylene diamine, diethylene triamine and triethylene tetramine.

An amount of the polyol or the polyamine to be used in the present invention is determined in accordance with an amount of coatings on microcapsules to be produced. An amount of the polyol for use in the present invention is usually from 5 to 80% by weight, preferably from 20 to 60% by weight, based on a weight of coatings on the microcapsules. An amount of the polyamine for use in the present invention is usually from 5 to 80% by weight, preferably from 20 to 60% by weight, based on a weight of coatings on the microcapsules.

A weight of the aqueous solution to be used in the second step is usually 0.8 to 2 times larger than a weight of the mixture obtained in the first step. As water to be used in the second step, deionized water is preferably used, and it optionally may be admixed with a thickener.

Examples of the thickener include natural polysaccharides such as Xanthan gum, Rhamsan gum, locust bean gum, carrageenan and Welan gum; synthesized polymers such as sodium polyacrylate; semisynthesized polymers such as carboxymethyl cellulose; mineral powder such as magnesium aluminum silicate, smectite, bentonite, hectorite and dry silica; and alumina sol.

In the second step, to form the liquid droplets in the aqueous solution, for example, the mixture obtained in the first step is added to the aqueous solution which contains a polyol or a polyamine; and then, the resulting mixture is stirred with a stirrer. Examples of the stirrer usable in this step include a propeller type aerator, a turbine agitator and a high-speed shearing stirrer. Specific examples of the stirrer include T.K. Homo Mixer, T.K. Homomic Line Flow, T.K. Pipeline Homo Mixer and T.K. FILMIX from PRIMIX Corporation; CLEARMIX from Mtechnique; POLYTRON homizinizer and MEGTRON homodinizer from KINEMATICA; and Supraton from TSUKISIMA KIKAI CO., LTD.

Particle diameters of the microcapsules to be produced by the process of the present invention are substantially equal to the particle diameters of the liquid droplets prepared in the second step. The particle diameters of the liquid droplets prepared in the second step and those of the microcapsules of the present invention are usually from 1 to 80 µm, preferably from 5 to 50 µm, in terms of volume median diameter.

The liquid droplets in the aqueous solution obtained in the second step are the polyisocyanate dissolved in the constitutive component (b). For this reason, the polyisocyanate in the liquid droplets and the polyol or the polyamine in the aqueous solution are polymerized at the interfaces of the liquid droplets. As a result, microcapsules which are the liquid droplets having coatings of a polyurethane or a polyurea formed thereon are obtained as an aqueous suspension in which such microcapsules are suspended.

When the resin which forms the coatings is a polyurethane resin, for example, the aqueous dispersion of the liquid droplets obtained in the second step is heated to a temperature of from 40 to 80° C. under stirring and is then kept at the same temperature for about 0.5 to about 48 hours to thereby form coatings of the polyurethane resin around the liquid droplets. When the resin which forms the coatings is a polyurea resin, for example, the aqueous dispersion of the liquid droplets is adjusted to be neutral or weak-alkaline and is then maintained at a temperature of from 0 to 50° C. for about 0.5 to about 48 hours to thereby form coatings of the polyurea resin around the liquid droplets.

By the above-described production process, a microcapsule formulation as the aqueous suspension-like composition can be produced. This microcapsule formulation is subjected to centrifugal separation, filtration or spray drying to obtain a powdery microcapsule formulation. Microcapsule formulations according to the present invention include aqueous suspension-like compositions and powdery formulations.

The microcapsule formulation of the present invention which is the aqueous suspension-like composition produced by the above-described process, optionally, may be further admixed with a thickener, an antifreezing admixture, an antiseptic, a specific gravity adjuster, a pH adjuster and water. In this case, the microcapsule formulation, i.e., the aqueous suspension-like composition, of the present invention produced by the above-described process contains, for example, 0.1 to 30% by weight of the agricultural chemical compound.

Examples of the thickener may be the same ones as listed above. An example of the antifreezing admixture is propylene glycol. Examples of the antiseptic include p-hydroxy benzoate; isothiazoline derivatives such as 5-chloro-2-methyl-4-isothiazoline-3-one and 2-methyl-4-isothiazoline-3-one; 2-bromo-2-nitropropane-1,3-diol; and salicylic acid derivatives. Specific examples of the antiseptic are Biohope L from K.I. CHEMICAL INDUSTRY CO., LTD. and Proxel GXL from Asibia Co., Ltd. Examples of the specific gravity adjuster are water-soluble salts such as sodium sulfate; and water-soluble compounds such as urea. Examples of the pH adjuster include disodium hydrogenphosphate, dipotassium hydrogenphosphate and sodium hydroxide.

In case where the agricultural chemical compound is an insecticidal active ingredient, an agricultural chemical composition which contains the microcapsules of the present invention is sprayed onto insect pests or a living area thereof at a rate of about 0.1 to about 1,000 g/1,000 m$^2$, preferably about 1 to about 100 g/1,000 m$^2$, in terms of the agricultural chemical compound.

Embodiments of the microcapsule formulation produced by the production process of the present invention will be described below.

That is, the following are provided as embodiments.

A microcapsule formulation produced by a process comprising the steps of maintaining a mixture of an agricultural chemical compound (the constitutive component (a)), at least one kind selected from the group consisting of ester compounds and aromatic hydrocarbon compounds (the constitutive component (b)), except for the compounds of the formula (I):

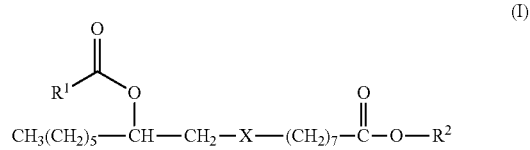

(wherein X represents —CH$_2$—CH$_2$— or —CH=CH—; R$^1$ represents a C$_1$-C$_4$ alkyl group; and R$^2$ represents a C$_1$-C$_4$ alkyl group) and a polyisocyanate (the constitutive component (c)) at a temperature of from 20 to 80° C. for 3 hours or longer; and adding the mixture to an aqueous solution which contains a polyol or a polyamine to form liquid droplets of the mixture in the aqueous solution; and forming coatings of a polyurethane or a polyurea around the liquid droplets, to thereby obtain the microcapsule formulation (hereinafter referred to as a microcapsule formulation of the present invention).

A microcapsule formulation of the present invention, containing microcapsules in which a ratio of a total volume of microcapsules with particle diameters of 5 µm or less to a total volume of the entire microcapsules is less than 20%; and in which a ratio of a total volume of microcapsules with particle diameters of 50 µm or more thereto is less than 20%.

A microcapsule formulation of the present invention, containing microcapsules in which a ratio of a total volume of microcapsules with particle diameters of 5 µm or less to a total volume of the entire microcapsules is less than 20%; in which a ratio of a total volume of microcapsules with particle diameters of 50 µm or more thereto is less than 20%; and in which a volume median diameter/a coating thickness is from 25 to 150.

A microcapsule formulation of the present invention, containing microcapsules in which a ratio of a total volume of microcapsules with particle diameters of 5 µm or less to a total volume of the entire microcapsules is less than 20%; in which a ratio of a total volume of microcapsules with particle diameters of 50 µm or more thereto is less than 20%; and in which coatings are of a polyurethane.

A microcapsule formulation of the present invention, containing microcapsules in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

A microcapsule formulation of the present invention, containing microcapsules in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; and in which a ratio of a total volume of microcapsules with particle diameters of 50 μm or more thereto is less than 20%.

A microcapsule formulation of the present invention, containing microcapsules in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which a volume median diameter/a coating thickness is from 25 to 150.

A microcapsule formulation of the present invention, containing microcapsules in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which coatings are of a polyurethane.

A microcapsule formulation of the present invention, containing microcapsules in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

A microcapsule formulation of the present invention, containing microcapsules in which an isothiazoline derivative is contained as an antiseptic; in which a ratio of a total volume of microcapsules with particle diameters of 5 μm or less to a total volume of the entire microcapsules is less than 20%; and in which a ratio of a total volume of microcapsules with particle diameters of 50 μm or more thereto is less than 20%.

A microcapsule formulation of the present invention, containing microcapsules in which an isothiazoline derivative is contained as an antiseptic; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which a volume median diameter/a coating thickness is from 25 to 150.

A microcapsule formulation of the present invention, containing microcapsules in which an isothiazoline derivative is contained as an antiseptic; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which coatings are of a polyurethane.

A microcapsule formulation of the present invention, containing microcapsules in which an isothiazoline derivative is contained as an antiseptic; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

A microcapsule formulation of the present invention, containing microcapsules in which an isothiazoline derivative is contained as an antiseptic; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; and in which a ratio of a total volume of microcapsules with particle diameters of 50 μm or more thereto is less than 20%.

A microcapsule formulation of the present invention, containing microcapsules in which an isothiazoline derivative is contained as an antiseptic; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which a volume median diameter/a coating thickness is from 25 to 150.

A microcapsule formulation of the present invention, containing microcapsules in which an isothiazoline derivative is contained as an antiseptic; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which coatings are of a polyurethane.

A microcapsule formulation of the present invention, containing microcapsules in which an isothiazoline derivative is contained as an antiseptic; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

A microcapsule formulation of the present invention, containing microcapsules in which an isothiazoline derivative as an antiseptic and a pH adjuster are contained; in which a ratio of a total volume of microcapsules with particle diameters of 5 μm or less to a total volume of the entire microcapsules is less than 20%; and in which a ratio of a total volume of microcapsules with particle diameters of 50 μm or more thereto is less than 20%.

A microcapsule formulation of the present invention, containing microcapsules in which an isothiazoline derivative as an antiseptic and a pH adjuster are contained; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which a volume median diameter/a coating thickness is from 25 to 150.

A microcapsule formulation of the present invention, containing microcapsules in which an isothiazoline derivative as an antiseptic and a pH adjuster are contained; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which coatings are of a polyurethane.

A microcapsule formulation of the present invention, containing microcapsules in which an isothiazoline derivative as an antiseptic and a pH adjuster are contained; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

A microcapsule formulation of the present invention, containing microcapsules in which an isothiazoline derivative as an antiseptic and a pH adjuster are contained; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; and in which a ratio of a total volume of microcapsules with particle diameters of 50 μm or more thereto is less than 20%.

A microcapsule formulation of the present invention, containing microcapsules in which an isothiazoline derivative as an antiseptic and a pH adjuster are contained; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which a volume median diameter/a coating thickness is from 25 to 150.

A microcapsule formulation of the present invention, containing microcapsules in which an isothiazoline derivative as an antiseptic and a pH adjuster are contained; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; and in which coatings are of a polyurethane.

A microcapsule formulation of the present invention, containing microcapsules in which an isothiazoline derivative as an antiseptic and a pH adjuster are contained; in which a weight ratio of the constitutive component (a) to the constitutive component (b) is from 20/100 to 40/100; in which a ratio of a total volume of microcapsules with particle diameters of 5 μm or less to a total volume of the entire microcapsules is less than 20%; in which a ratio of a total volume of microcapsules with particle diameters of 50 μm or more thereto is less than 20%; in which a volume median diameter/a coating thickness is from 25 to 150; and in which coatings are of a polyurethane.

EXAMPLES

The present invention will be described in more detail by way of Production Examples and Test Examples which however should not be construed as limiting the scope of the present invention in any way.

Production Example 1

Clothianidin (250 g) and diisobutyl adipate (VINYCIZER 40 manufactured by Kao Corporation) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.4 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.2 μm. A ratio of a total volume of clothianidin particles with particle diameters of 10 μm or more to a total volume of the entire clothianidin particles was 1.3%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 40° C. for 24 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 1).

A volume median diameter of the resultant microcapsules was 21.3 μm. A ratio of a total volume of microcapsules with particle diameters of 5 μm or less to a total volume of the entire microcapsules was 10.8%; and a ratio of a total volume of microcapsules with particle diameters of 50 μm or more thereto was 0%.

Production Example 2

Clothianidin (250 g) and diisobutyl adipate (VINYCIZER 40 manufactured by Kao Corporation) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.4 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.4 µm. A ratio of a total volume of clothianidin particles with particle diameters of 10 µm or more to a total volume of the entire clothianidin particles was 1.6%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 60° C. for 6 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 2).

A volume median diameter of the resultant microcapsules was 20.8 µm. A ratio of a total volume of microcapsules with particle diameters of 5 µm or less to a total volume of the entire microcapsules was 10.3%; and a ratio of a total volume of microcapsules with particle diameters of 50 µm or more thereto was 0%.

Production Example 3

Clothianidin (250 g) and methyl naphthalene (Solvesso 200 manufactured by Exxon) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.5 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.5 µm. A ratio of a total volume of clothianidin particles with particle diameters of 10 µm or more to a total volume of the entire clothianidin particles was 1.8%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 40° C. for 24 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 3).

A volume median diameter of the resultant microcapsules was 19.9 µm. A ratio of a total volume of microcapsules with particle diameters of 5 µm or less to a total volume of the entire microcapsules was 9.2%; and a ratio of a total volume of microcapsules with particle diameters of 50 µm or more thereto was 0.2%.

Production Example 4

Clothianidin (250 g) and methyl naphthalene (Solvesso 200 manufactured by Exxon) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.5 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.5 µm. A ratio of a total volume of clothianidin particles with particle diameters of 10 µm or more to a total volume of the entire clothianidin particles was 1.8%.

The mixture 1-3 (100 g) was admixed with a polyisocyanate (Sumidule L-75 manufactured by Sumika Bayer Urethane Co., Ltd.) (9.8 g) at 40° C. to obtain a mixture (hereinafter referred to as a mixture 1-4). Then, the mixture 1-4 was maintained at 60° C. for 6 hours. Herein, the resulting mixture was referred to as a mixture 1-5.

An aqueous solution was prepared by adding ethylene glycol (5.6 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 4).

A volume median diameter of the resultant microcapsules was 21.3 μm. A ratio of a total volume of microcapsules with particle diameters of 5 μm or less to a total volume of the entire microcapsules was 10.2%; and a ratio of a total volume of microcapsules with particle diameters of 50 μm or more thereto was 0.2%.

Production Example 5

Clothianidin (250 g) and diisodecyl adipate (VINYCIZER 50 manufactured by Kao Corporation) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. The resulting mixture was referred to as a mixture 1-2. A volume median diameter of the clothianidin particles in the mixture 1-2 was 0.5 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.9 μm. A ratio of a total volume of clothianidin particles with particle diameters of 10 μm or more to a total volume of the entire clothianidin particles was 3.4%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 40° C. for 24 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 5).

A volume median diameter of the resultant microcapsules was 20.4 μm. A ratio of a total volume of microcapsules with particle diameters of 5 μm or less to a total volume of the entire microcapsules was 8.7%; and a ratio of a total volume of microcapsules with particle diameters of 50 μm or more thereto was 0.1%.

Production Example 6

Clothianidin (250 g) and diisodecyl adipate (VINYCIZER 50 manufactured by Kao Corporation) (750 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.5 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.5 μm. A ratio of a total volume of clothianidin particles with particle diameters of 10 μm or more to a total volume of the entire clothianidin particles was 1.8%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 60° C. for 6 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 6).

A volume median diameter of the resultant microcapsules was 22.6 μm. A ratio of a total volume of microcapsules with particle diameters of 5 μm or less to a total volume of the entire microcapsules was 7.6%; and a ratio of a total volume of microcapsules with particle diameters of 50 μm or more thereto was 0.3%.

Production Example 7

Clothianidin (250 g), diisodecyl adipate (VINYCIZER 50 manufactured by Kao Corporation) (375 g) and diisobutyl adipate (VINYCIZER 40 manufactured by Kao Corporation) (375 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.5 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.7 μm. A ratio of a total volume of clothianidin particles with particle diameters of 10 μm or more to a total volume of the entire clothianidin particles was 1.8%.

The mixture 1-3 (100 g) was admixed with a polyisocyanate (Sumidule L-75 manufactured by Sumika Bayer Urethane Co., Ltd.) (21.6 g) at 40° C. to obtain a mixture (hereinafter referred to as a mixture 1-4). Then, the mixture 1-4 was maintained at 40° C. for 24 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 7).

A volume median diameter of the resultant microcapsules was 20.7 μm. A ratio of a total volume of microcapsules with particle diameters of 5 μm or less to a total volume of the entire microcapsules was 8.4%; and a ratio of a total volume of microcapsules with particle diameters of 50 μm or more thereto was 0.3%.

Production Example 8

Clothianidin (250 g), diisodecyl adipate (VINYCIZER 50 manufactured by Kao Corporation) (375 g) and diisobutyl adipate (VINYCIZER 40 manufactured by Kao Corporation) (375 g) were mixed to obtain a mixture (hereinafter referred to as a mixture 1-1). The mixture 1-1 was stirred in a rotor-stator homogenizer (POLYTRON® PT6100 manufactured by KINEMATICA AG) to pulverize the clothianidin in the mixture 1-1 for about 10 minutes. Herein, the resulting mixture was referred to as a mixture 1-2. A volume median diameter of the clothianidin particles in the mixture 1-2 was 0.6 mm.

The mixture 1-2 was added to DYNO-MILL (with a vessel size of 600 ml, manufactured by WILLY A. BACHOFEN AG. MASHINENFABRIK, charged with globular glass beads with a diameter of 1 mm (1,150 g); a rotating speed of a stirring blade: 12 m/sec. in peripheral speed) at a rate of 3 L/hr. so as to further pulverize the clothianidin particles. Herein, the resulting mixture was referred to as a mixture 1-3. A volume median diameter of the clothianidin particles in the mixture 1-3 was 2.3 μm. A ratio of a total volume of clothianidin particles with particle diameters of 10 μm or more to a total volume of the entire clothianidin particles was 0%.

The mixture 1-3 (100 g) was admixed with a polyisocyanate (Sumidule L-75 manufactured by Sumika Bayer Urethane Co., Ltd.) (21.6 g) at 45° C. to obtain a mixture (hereinafter referred to as a mixture 1-4). Then, the mixture 1-4 was maintained at 60° C. for 6 hours. Herein, the resulting mixture was referred to as a mixture 1-5.

An aqueous solution was prepared by adding ethylene glycol (12.4 g) and gum arabic (Arabic Cole SS manufactured by SAN-EI YAKUHIN BOEKI CO., LTD.) (12.6 g) to water (deionized water) (108.8 g). The entire amount of this aqueous solution was mixed with the entire amount of the mixture 1-5 to obtain a mixture (hereinafter referred to as a mixture 1-6).

The mixture 1-6 was stirred at room temperature with T.K. auto-homomixer (a homogenizer manufactured by PRIMIX; a number of revolutions: 9,000 rpm) to form liquid droplets in the aqueous solution (this mixture being referred to as a mixture 1-7).

The mixture 1-7 was stirred at 60° C. for 24 hours to obtain an aqueous suspended composition which contained microcapsules enveloping clothianidin (hereinafter referred to as an aqueous suspended composition 8).

A volume median diameter of the resultant microcapsules was 18.9 μm. A ratio of a total volume of microcapsules with particle diameters of 5 μm or less to a total volume of the entire microcapsules was 11.4%; and a ratio of a total volume of microcapsules with particle diameters of 50 μm or more thereto was 0%.

Comparative Production Example 1

Production Example 1 was repeated to obtain an aqueous suspended composition (hereinafter referred to as a comparative aqueous suspended composition 1), except that the procedure of maintaining the mixture 1-4 at 40° C. for 24 hours in Production Example 1 (the resulting mixture being referred to as a mixture 1-5) was changed to a procedure of maintaining the mixture 1-4 at 25° C. for 0.3 hour (the resulting mixture being referred to as a mixture 1-5).

A volume median diameter of the resultant microcapsules was 20.8 μm, and a ratio of a total volume of microcapsules with particle diameters of 5 μm or less to a total volume of the entire microcapsules is 8.1%, and a ratio of a total volume of microcapsules with particle diameters of 50 μm or more thereto is 0%.

Comparative Production Example 2

Production Example 3 was repeated to obtain an aqueous suspended composition (hereinafter referred to as a comparative aqueous suspended composition 2), except that the procedure of maintaining the mixture 1-4 at 40° C. for 24 hours in Production Example 3 (the resulting mixture being referred to as a mixture 1-5) was changed to a procedure of maintaining the mixture 1-4 at 25° C. for 0.3 hour (the resulting mixture being referred to as a mixture 1-5).

A volume median diameter of the resultant microcapsules was 21.2 μm, and a ratio of a total volume of microcapsules with particle diameters of 5 μm or less to a total volume of the entire microcapsules is 8.4%, and a ratio of a total volume of microcapsules with particle diameters of 50 μm or more thereto is 0%.

Comparative Production Example 3

Production Example 5 was repeated to obtain an aqueous suspended composition (hereinafter referred to as a comparative aqueous suspended composition 3), except that the procedure of maintaining the mixture 1-4 at 40° C. for 24 hours in Production Example 5 (the resulting mixture being referred to as a mixture 1-5) was changed to a procedure of maintaining the mixture 1-4 at 25° C. for 0.3 hour (the resulting mixture being referred to as a mixture 1-5).

A volume median diameter of the resultant microcapsules was 22.3 μm, and a ratio of a total volume of microcapsules with particle diameters of 5 μm or less to a total volume of the entire microcapsules is 7.3%, and a ratio of a total volume of microcapsules with particle diameters of 50 μm or more thereto is 0%.

Comparative Production Example 4

Production Example 7 was repeated to obtain an aqueous suspended composition (hereinafter referred to as a comparative aqueous suspended composition 4), except that the procedure of maintaining the mixture 1-4 at 40° C. for 24 hours in Production Example 7 (the resulting mixture being referred to as a mixture 1-5) was changed to a procedure of maintaining the mixture 1-4 at 25° C. for 0.3 hour (the resulting mixture being referred to as a mixture 1-5).

A volume median diameter of the resultant microcapsules was 19.6 μm, and a ratio of a total volume of microcapsules with particle diameters of 5 μm or less to a total volume of the entire microcapsules is 8.6%, and a ratio of a total volume of microcapsules with particle diameters of 50 μm or more thereto is 0%.

Test Examples

Each of the aqueous suspended compositions obtained in Production Examples and Comparative Production Examples (each 0.5 g) was mixed with water (99.5 g). This mixture was left to stand alone at room temperature for 2 hours. After that, the mixture was subjected to centrifugal separation at 3,000 rpm for 15 minutes in a centrifugal separator. About 1 mL of the supernatant obtained after the centrifugal separation was taken out, and 10 μL of the supernatant taken out of the same was analyzed by high-performance liquid chromatography to determine an amount of clothianidin. Based on this analyzed value of clothianidin, an amount of clothianidin contained in the supernatant and an amount of clothianidin enveloped in the microcapsules were calculated. A ratio of an amount of clothianidin enveloped in the microcapsules found after the test, to an amount of clothianidin enveloped in the microcapsules found before the test is shown in Table 1.

TABLE 1

|  | Ratio of amount of clothianidin in microcapsules after the test (%) |
| --- | --- |
| Aqueous suspended composition 1 | 70 |
| Aqueous suspended composition 2 | 68 |
| Comparative aqueous suspended composition 1 | 27 |

TABLE 1-continued

|  | Ratio of amount of clothianidin in microcapsules after the test (%) |
| --- | --- |
| Aqueous suspended composition 3 | 61 |
| Aqueous suspended composition 4 | 69 |
| Comparative aqueous suspended composition 2 | 19 |
| Aqueous suspended composition 5 | 60 |
| Aqueous suspended composition 6 | 66 |
| Comparative aqueous suspended composition 3 | 16 |
| Aqueous suspended composition 7 | 67 |
| Aqueous suspended composition 8 | 71 |
| Comparative aqueous suspended composition 4 | 18 |

According to the production process of the present invention, microcapsules further delayed in timing for releasing an agricultural chemical compound can be produced.

The invention claimed is:

1. A process for producing a microcapsule formulation, comprising the steps of
   (1) maintaining a mixture of the following constitutive components (a), (b) and (c) at a temperature of from 40 to 80° C. for 3 hours or longer;
   (2) adding the resulting mixture to an aqueous solution which contains a polyol or a polyamine, to form liquid droplets of the mixture in the aqueous solution;
   (3) forming coatings of a polyurethane or a polyurea around the liquid droplets:
      the constitutive component (a): an agricultural chemical compound, wherein the agricultural chemical compound is a neonicotinoid compound;
      the constitutive component (b): at least one kind selected from the group consisting of diisobutyl adipate, dihexyl adipate, bis(2-ethylhexyl) adipate, dioctyl adipate, diisononyl adipate, didecyl adipate, diisodecyl adipate, methyl naphthalene, dimethyl naphthalene, and ethyl naphthalene; and
      the constitutive compound (c): a polyisocyanate.

2. The process according to claim 1, wherein a weight ratio of the constitutive component (a) to the constitutive component (b) is from 10/100 to 100/100.

3. The process according to claim 1, wherein the constitutive component (b) is at least one kind selected from the group consisting of diisobutyl adipate, diisodecyl adipate and methyl naphthalene.

4. The process according to claim 1, wherein the agricultural chemical compound is clothianidin.

* * * * *